United States Patent
Auvin et al.

(10) Patent No.: US 7,659,266 B2
(45) Date of Patent: Feb. 9, 2010

(54) AMIDINE DERIVATIVES AND THEIR APPLICATIONS AS A MEDICAMENT

(75) Inventors: Serge Auvin, Palaiseau (FR); Dennis Bigg, Gif sur Yvette (FR); Pierre-Etienne Chabrier De Lassauniere, Paris (FR); Bernadette Pignol, Paris (FR)

(73) Assignee: S.C.R.A.S., Paris (FR)

( * ) Notice: Subject to any disclaimer, the term of this patent is extended or adjusted under 35 U.S.C. 154(b) by 0 days.

(21) Appl. No.: 12/090,991

(22) PCT Filed: Oct. 18, 2006

(86) PCT No.: PCT/FR2006/002338

§ 371 (c)(1),
(2), (4) Date: Jul. 30, 2008

(87) PCT Pub. No.: WO2007/045761

PCT Pub. Date: Apr. 26, 2007

(65) Prior Publication Data

US 2009/0018120 A1    Jan. 15, 2009

(30) Foreign Application Priority Data

Oct. 21, 2005    (FR) .................... 05 10751
Mar. 7, 2006    (FR) .................... 06 01999

(51) Int. Cl.
*C07D 279/20*    (2006.01)
*C07D 417/12*    (2006.01)
*A61K 31/5415*    (2006.01)

(52) U.S. Cl. .................... 514/225.2; 544/35; 544/38

(58) Field of Classification Search .................... 544/35, 544/38; 514/225.2
See application file for complete search history.

(56) References Cited

FOREIGN PATENT DOCUMENTS

| WO | WO01/32654 A1 | 5/2001 |
|---|---|---|
| WO | WO2005/056551 A2 | 6/2005 |
| WO | WO2005/092345 A1 | 10/2005 |
| WO | WO2007/045761 A1 | 4/2007 |

OTHER PUBLICATIONS

Cecil Textbook of Medicine (20th Edition, vol. 2, 1996, pp. 1739-1747).*
R. I. Souhami and J. Moxham ed.; "Textbook of Medicine" (Oct. 2002, Churchill Livingston, UK), see Chapter 4 p. 79-104.*

* cited by examiner

*Primary Examiner*—Kahsay T Habte
(74) *Attorney, Agent, or Firm*—Hunton & Williams LLP

(57) ABSTRACT

The invention concerns amidine derivatives of general formula (I) exhibiting an inhibitory activity of calpains and/or a trapping activity of reactive forms of oxygen.

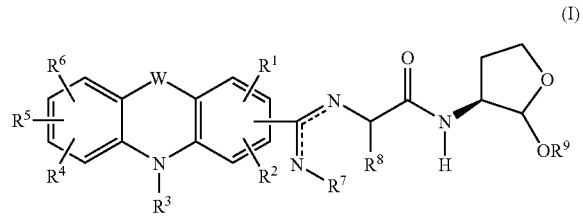

27 Claims, No Drawings

AMIDINE DERIVATIVES AND THEIR APPLICATIONS AS A MEDICAMENT

A subject of the present invention is amidine derivatives having an inhibitory activity on calpains and/or a trapping activity on reactive oxygen species (ROS). The invention also relates to methods for their preparation, pharmaceutical preparations containing them and their use for therapeutic purposes, in particular as inhibitors of calpains and selective or non-selective ROS traps.

Given the potential role of calpains and ROS's in physiopathology, the new derivatives according to the invention can produce beneficial or favourable effects in the treatment of pathologies involving these enzymes and/or these radicular species, and in particular:
- inflammatory and immunological diseases such as for example rheumatoid arthritis, pancreatitis, multiple sclerosis, inflammation of the gastrointestinal tract (for example ulcerative or non-ulcerative colitis, Crohn's disease),
- cardio-vascular and/or cerebro-vascular diseases comprising, for example, arterial hypertension, septic shock, cardiac or cerebral infarction of ischemic or haemorrhagic origin, ischemias as well as disorders linked to platelet aggregation.
- disorders of the central or peripheral nervous system such as, for example, neurodegenerative diseases where there can, in particular, be mentioned trauma to the brain or spinal cord, sub-arachnoid hemorrhages, epilepsy, ageing, senile dementia, including Alzheimer's disease, Huntington's chorea, Parkinson's disease, peripheral neuropathies,
- cachexia,
- sarcopenia,
- hearing loss, in particular hearing loss caused by presbycusis, acoustic trauma, or by administration of a medicament such as antibiotics, such as, for example, gentamycin, anti-cancer medicaments such as, for example, cisplatin, non-steroidal anti-inflammatories such as, for example, salicylic acid or ibuprofen derivatives, diuretics such as, for example, furosemide, anti-ulcer medicaments such as, for example, cimetidine or omeprazole, anticonvulsive agents such as, for example, carbamazepine or valproic acid,
- osteoporosis,
- muscular dystrophies, such as, for example, in particular Duchenne's muscular dystrophy, Becker's muscular dystrophy, myotonic muscular dystrophy or Steiner's disease, congenital muscular dystrophy, limb-girdle muscular dystrophy and facioscapulohumeral muscular dystrophy,
- proliferative non-cancerous diseases such as, for example, atherosclerosis or recurrence of stenosis,
- cataract,
- organ transplantations,
- auto-immune or viral diseases such as, for example, lupus, AIDS, parasitic or viral infections, diabetes and its complications,
- cancer and cancerous proliferative diseases.
- all the pathologies characterized by excessive production of ROS's and/or activation of calpain.

In all these pathologies, there is experimental evidence demonstrating the involvement of ROS's (Free Radic. Biol. Med. (1996) 20, 675-705; Antioxid. Health. Dis. (1997) 4 (Handbook of Synthetic Antioxidants), 1-52) as well as the involvement of calpains (Trends Pharmacol. Sci. (1994) 15, 412419; Drug News Perspect (1999) 12, 73-82). By way of example, cerebral lesions associated with cerebral infarction or experimental cranial trauma are reduced by antioxidants (Acta. Physiol. Scand. (1994) 152, 349-350; J. Cereb. Blood Flow Metabol. (1995) 15, 948-952; J Pharmacol Exp Ther (1997) 2, 895-904) as well as by inhibitors of calpains (Proc Natl Acad Sci USA (1996) 93, 3428-33; Stroke, (1998) 29, 152-158; Stroke (1994) 25, 2265-2270).

In order to fulfil the requirements of the industry, it has become necessary to find other compounds having an inhibitory activity on calpains and/or a trapping activity on reactive oxygen species.

Thus the problem that the invention aims to solve is to provide novel compounds having an inhibitory activity on calpains and/or a trapping activity on reactive oxygen species.

Unexpectedly, the inventors have shown that the compounds of general formula (I) described hereafter or their salts, in racemic form, diastereoisomers or all combinations of these forms have an inhibitory activity on calpains and/or a trapping activity on reactive oxygen species.

An advantage of the invention is that it can be implemented in all industries, in particular the pharmaceutical, veterinary, cosmetic, and food industries, as well as in agricultural fields.

The compounds according to the invention or their salts have increased solubility in biological media, in particular in aqueous media.

Other advantages and characteristics of the invention will become clearly apparent on reading the following description and examples which are given purely by way of illustration and are not limitative.

A subject of the present invention is thus a compound of general formula (I) or its salt,

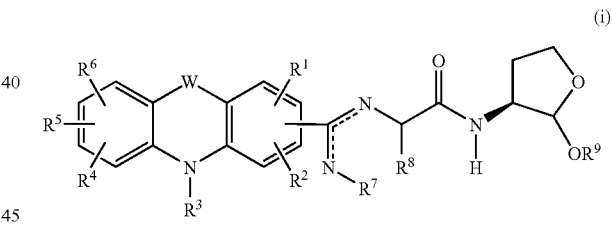

in racemic form, diastereoisomers or all combinations of these forms in which:

$R^1$, $R^2$, $R^4$, $R^5$ and $R^6$ represent, independently, a hydrogen atom, halogen atom, the OH group, an alkyl, alkoxy, cyano, nitro, amino, alkylamino radical or carboxylic acid;

$R^3$ represents a hydrogen atom, an alkyl radical or a —$COR^{10}$ group;

$R^{10}$ represents a hydrogen atom or an alkyl, alkoxy, aryl radical, or a heterocyclic radical;

W represents an oxygen atom or a sulphur atom or —W— represents a bond;

$R^7$ represents a hydrogen atom or an alkyl radical;

$R^8$ represents a hydrogen atom, a haloalkyl or alkenyl radical, a cycloalkyl radical, a linear or branched alkyl radical, substituted or not, which when it is substituted carries a chemical function such as carboxylic acid, amino, alcohol, guanidine, amidine, thiol, thioether, thioester, alkoxy, heterocyclic or carboxamide;

$R^9$ represents a hydrogen atom, an alkyl, aryl, arylalkyl, bisarylalkyl radical, a heterocyclic radical, a heterocyclic alkyl radical or a —$COR^{10}$ group;

it being understood that:

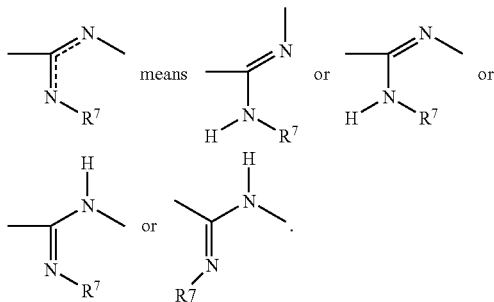

Preferably, the compound according to the invention has a radical $R^1$ which is a hydrogen atom.

Preferably, the compound according to the invention has an $R^2$ radical which is a hydrogen atom.

Preferably, the compound according to the invention has an $R^3$ radical which is a hydrogen atom.

Preferably, the compound according to the invention has an $R^4$ radical which is a hydrogen atom.

Preferably, the compound according to the invention has an $R^5$ radical which is a hydrogen atom.

Preferably, the compound according to the invention has an $R^6$ radical which is a hydrogen atom.

Preferably, the compound according to the invention has an $R^7$ radical which is a hydrogen atom.

Preferably, the compound according to the invention has an $R^8$ radical which is an isobutyl radical.

Preferably, the atom W of the compound according to the invention is a sulphur atom.

Preferably, the compound according to the invention has an $R^9$ radical which is a hydrogen atom.

Preferably, the compound according to the invention has an $R^9$ radical which is an acetyl radical.

Preferably, the compound according to the invention has an $R^9$ radical which is a methyl radical.

Preferably, the compound according to the invention has an $R^9$ radical which is a benzyl radical.

Preferably, the compound according to the invention has an $R^9$ radical which is a naphthylmethyl radical.

By alkyl, unless defined otherwise, is meant a linear or branched alkyl radical containing 1 to 12 carbon atoms, and preferably 1 to 6 carbon atoms, even more preferentially 1 to 4 carbon atoms. By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals.

By haloalkyl, is meant an alkyl radical of which at least one of the hydrogen atoms is substituted by a halogen atom. By haloalkyl, is meant for example the —$CF_3$, —$CHF_2$ or —$CH_2Cl$ radical.

By alkenyl, unless defined otherwise, is meant a linear or branched alkenyl radical having at least 1 unsaturation and containing 2 to 12 carbon atoms, and preferably 2 to 6 carbon atoms.

By alkoxy, unless defined otherwise, is meant an R—O— radical the carbon-containing chain R of which is linear or branched and has 1 to 6 carbon atoms.

By cycloalkyl, unless defined otherwise, is meant a saturated carbocyclic radical containing 3 to 7 carbon atoms. By cycloalkyl containing 3 to 7 carbon atoms, is meant in particular a cyclohexyl radical.

By aryl, unless defined otherwise, is meant an aromatic carbocyclic radical, having preferably 1 to 3 fused rings. By aryl, is meant in particular the phenyl, naphthyl and phenantryl radicals, preferably the phenyl and naphthyl radicals and more preferentially the phenyl radical.

By arylalkyl radicals is meant arylalkyl radicals of which their component alkyl and aryl radicals respectively have the meanings given above, it being understood that the aryl radical is attached to the (I) or (SI) molecule via an alkyl radical.

By bisarylalkyl is meant in the sense of the present invention an aromatic carbocyclic radical comprising at least 2 rings, at least one of which is aromatic, and comprising at most 14 carbon atoms, preferably at most 10 carbon atoms, it being understood that the bisarylalkyl radical is attached to the (I) or (SI) molecule via an alkyl radical.

By heterocyclic, is meant in the sense of the present invention a cyclic radical which is aromatic or not comprising 1 to 14 atoms, these atoms being chosen from carbon, nitrogen, oxygen or sulphur, or one of their compounds. It is understood that the heterocyclic radical can be partially unsaturated. By heterocyclic, is meant for example a heteroaryl radical or a heterocycloakyl radical.

By heterocyclic alkyl, is meant in the sense of the present invention a heterocyclic alkyl radical of which the heterocyclic and alkyl radicals which comprise them have the meanings indicated above and the heterocyclic radical of which is attached to the (I) or (SI) molecule via a an alkyl radical.

By halogen atom is meant an atom chosen from fluorine, chlorine, bromine or iodine atoms.

By amino, is meant in the sense of the present invention an —$NH_2$ radical.

By alkylamino, is meant in the meaning of the present invention an —NRH or —$N(R)_2$ radical with R being an alkyl radical as defined above.

The following examples indicate the protective groups which can protect functions carried by the $R^8$ radical:

methyl, ethyl, tert-butyl or benzyl esters can protect acid functions;

benzyl or fluorenylmethyl tert-butyl carbamates can protect the amine functions;

acetamides can protect amine functions; and tert-butyl, benzyl, tetrahydropyrane or silyl ethers can protect alcohol functions; and acetyls can protect alcohol functions; and methyl thioethers or methyl thioesters can protect thiol functions.

In particular, the invention relates to a compound of general formula (I) chosen from the following compounds or their salts:

$N^2$-[imino(10H-phenothiazin-2-yl)methyl]-$N^1$-[(3S)-2-methoxytetrahydrofuran-3-yl]-L-leucinamide;

$N^1$-[(3S)-2-(benzyloxy)tetrahydrofuran-3-yl]-$N^2$-[imino (10H-phenothiazin-2-yl)methyl]-L-leucinamide;

$N^2$-[imino(10H-phenothiazin-2-yl)methyl]-$N^1$-[(3S)-2-(2-naphthylmethoxy) tetrahydrofuran-3-yl]-L-leucinamide;

(3S)-3-({N-[imino(10H-phenothiazin-2-yl)methyl]-L-leucyl}amino)tetrahydrofuran-2-yl acetate;

$N^1$-[(3S)-2-hydroxytetrahydrofuran-3-yl]-$N^2$-[imino(10H-phenothiazin-2-yl)methyl]-L-leucinamide.

The terminology used for the nomenclature of the compounds above is the English IUPAC terminology.

A subject of the present invention is also a compound of general formula (I) or its salt, as defined above, for use as a therapeutically active substance.

More particularly, the compounds according to the invention or their salts can be used as a therapeutically active substance for the treatment of pathologies characterized by an excessive production of ROS and/or an activation of calpains.

Even more particularly, the compounds according to the invention or their salts can be used as a therapeutically active substance for treating diseases and disorders chosen from the inflammatory or immunological diseases, cardiovascular diseases, cerebro-vascular diseases, central or peripheral nervous system disorders cachexia, sarcopenia, hearing loss, osteoporosis, muscular dystrophies, proliferative diseases whether cancerous or not, cataract, rejection reactions following organ transplantation, auto-immune diseases, viral diseases or cancer.

Preferably, a subject of the invention is a compound of general formula (I) or its salt, as defined above, for its use as a therapeutically active substance for the treatment of hearing loss or muscular dystrophies.

A subject of the present invention is also a medicament comprising at least one compound of general formula (I) as defined above, or one of its salts. Preferably, these are pharmaceutically acceptable salts of such compounds.

A subject of the present invention, as medicaments, is also the compounds of general formula (I) as defined above, or their pharmaceutically acceptable salts.

The invention also relates to pharmaceutical compositions containing at least one compound of general formula (I) as defined above, or at least one pharmaceutically acceptable salt of such a compound. Preferably the pharmaceutical compound comprises at least one pharmaceutically acceptable excipient. Preferably, the compound of general formula (I) as defined previously, or its salt, is contained in the pharmaceutically active composition as active ingredient.

By pharmaceutically acceptable salt, is meant in particular the addition salts of inorganic acids such as, for example, hydrochloride, hydrobromide, hydroiodide, sulphate, phosphate, diphosphate or nitrate or organic acids such as, for example, acetate, maleate, fumarate, tartrate, succinate, citrate, lactate, methanesulphonate, p-toluenesulphonate, benzenesulphonate, pamoate or stearate. For other examples of pharmaceutically acceptable salts, reference can be made to "Salt selection for basic drugs", *Int. J. Pharm.* (1986), 33, 201-217.

The compound of general formula (I) or its salt used according to the invention can be in solid form, for example, powders, granules, tablets, gelatin capsules, liposomes, or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine or wax.

The compound of general formula (I) according to the invention or its salt can also be presented in liquid form, for example, solutions, emulsions in the broad sense, gels, suspensions, sprays or syrups. Appropriate liquid supports can be for example water, organic solvents such as glycerol or glycols, as well as their mixtures, in varying proportions, in water.

The invention relates to moreover the use of a compound of general formula (I) as defined above, or a pharmaceutically acceptable salt of such a compound, for preparing a medicament intended to treat all the pathologies characterized by an excessive production of ROS and/or an activation of calpains, and in particular the diseases and disorders chosen from the inflammatory or immunological diseases, cardio-vascular diseases, cerebro-vascular diseases, disorders of the central or peripheral nervous system, cachexia, sarcopenia, hearing loss, osteoporosis, muscular dystrophies, proliferative diseases whether cancerous or not, cataract, rejection reactions following organ transplantation, auto-immune diseases, viral diseases or cancer.

The administration of a compound of general formula (I) according to the invention or its salt can be carried out by topical, oral, parenteral route, by intramuscular, sub-cutaneous injection, etc.

The dose of a product according to the present invention, to be provided for the treatment of the diseases or disorders mentioned above, varies according to the administration method, the age and body weight of the patient as well as the state of the latter, and will be decided definitively by the attending doctor or vet. Such a quantity determined by the attending doctor or vet is known here as the "therapeutically active quantity".

A subject of the invention is also a compound of general formula (SI) or its salt, (SI)

in the form of stereoisomers or their combinations in which:

W, $R^1$, $R^2$, $R^3$, $R^4$, $R^5$, $R^6$ and $R^7$ have the same meaning as for the compounds of formula I), and $R^{11}$ represents an alkyl, aryl, arylalkyl, bisarylalkyl radical, a heterocyclic radical or a heterocyclic alkyl radical.

A subject of the present invention is also compounds or their salts which are synthesis intermediates obtained during synthesis of the compounds of general formula (I), chosen from the following compounds:

Methyl 10H-phenothiazine-2-carbimidothioate;

$N^2$-[imino(10H-phenothiazin-2-yl)methyl]-$N^1$-[(3S)-2-methoxytetrahydrofuran-3-y i]-L-leucinamide;

$N^2$-[(9H-fluoren-9-ylmethoxy)carbonyl]-$N^1$-[(3S)-2-oxotetrahydrofuran-3-yl]-L-leucinamide;

$N^1$-[(3S)-2-(benzyloxy)tetrahydrofuran-3-yl]-$N^2$-[(9H-fluoren-9-ylmethoxy)carbonyl]-L-leucinamide;

$N^1$-[(3S)-2-(benzyloxy)tetrahydrofuran-3-yl]-L-leucinamide;

$N^1$-[(3S)-2-(benzyloxy)tetrahydrofuran-3-yl]-$N^2$-[imino(10H-phenothiazin-2-yl)methyl]-L-leucinamide;

$N^2$-[(9H-fluoren-9-ylmethoxy)carbonyl]-$N^1$-[(3S)-2-(2-naphthylmethoxy)tetrahydrofuran -3-yl]-L-leucinamide;

$N^1$-[(3S)-2-(2-naphthylmethoxy)tetrahydrofuran-3-yl]-L-leucinamide;

$N^2$-[imino(10H-phenothiazin-2-yl)methyl]-$N^1$-[(3S)-2-(2-naphthylmethoxy)tetrahydrofuran-3-yl]-L-leucinamide;

(3S)-3-(L-leucylamino)tetrahydrofuran-2-yl acetate;

(3S)-3-({N-[imino(10H-phenothiazin-2-yl)methyl]-L-leucyl}amino)tetrahydrofuran-2-yl acetate;

N-ethyl-10H-phenothiazine-2-carboxamide;

N-ethyl-10H-phenothiazine-2-carbothioamide;

Methyl N-ethyl-10H-phenothiazine-2-carbimidothioate.

The terminology used for the nomenclature of the compounds above is the English IUPAC terminology.

A subject of the present invention is also a compound or its salt which is one of the synthesis intermediates (SI) described above, for use as a therapeutically active substance. More particularly, these compounds according to the invention or their salts can be used as therapeutically active substances for the treatment of pathologies characterized by an excessive production of ROS and/or an activation of calpains.

Even more particularly, these compounds according to the invention or their salts, which are the synthesis intermediates (SI) described above, can be used as a therapeutically active substance for treating diseases and disorders chosen from the inflammatory or immunological diseases, cardiovascular diseases, cerebro-vascular diseases, central or peripheral nervous system disorders, cachexia, sarcopenia, hearing loss, osteoporosis, muscular dystrophies, proliferative diseases, whether cancerous or not, cataract, rejection reactions following organ transplantation, auto-immune diseases, viral diseases or cancer.

A subject of the present invention is also a medicament comprising at least one compound or its salt, which is one of the synthesis intermediates (SI) described above. Preferably these are pharmaceutically acceptable salts of such compounds.

A subject of the present invention, as medicaments, is also at least one compound or its pharmaceutically acceptable salt, which is one of the synthesis intermediates (SI) described above.

The invention also relates to pharmaceutical compositions containing at least one compound or its salt, which is one of the synthesis intermediates (SI) described above, or at least one pharmaceutically acceptable salt of such compound. Preferably, the pharmaceutical composition comprises at least one pharmaceutically acceptable vehicle. Preferably, the compound or its salt, which is one of the synthesis intermediates (SI) described above, is contained in the pharmaceutical composition as an active ingredient.

A subject of the invention is also the use of at least one compound or product of general formula (I) or one of the synthesis intermediates (SI) according to the invention or its salt in the pharmaceutical, veterinary, chemical, cosmetic, foodstuffs industries, as well as in agricultural fields.

Preparation of the Compounds of General Formula (I):

The compounds of general formula (I) according to the invention can be prepared according to the synthesis route shown in Diagram 1 below. The compounds of general formula (I) in which $R^9$ represents an alkyl, aryl, arylalkyl, bisarylalkyl radical, a heterocyclic radical, a heterocyclic alkyl radical or a —$COR^{10}$ group with $R^{10}$ representing a hydrogen atom or an alkyl, alkoxy, aryl radical, or a heterocyclic radical are known as the compounds of general formula $(I)_1$. The compounds of general formula (I) in which $R^9$ represents a hydrogen atom are known as the compounds of general formula $(I)_2$ in the remainder of the description. In Diagram 1 below, as well as Diagram 2, the meaning of W, $R^1$, $R^2$, $R^3$, $R^4$, $R^5$, $R^6$, $R^7$, $R^8$, $R^9$, $R^{10}$ and $R^{11}$ in the compounds of general formulae (II), (III), $(I)_1$ and $(I)_2$, is as previously stated in the description:

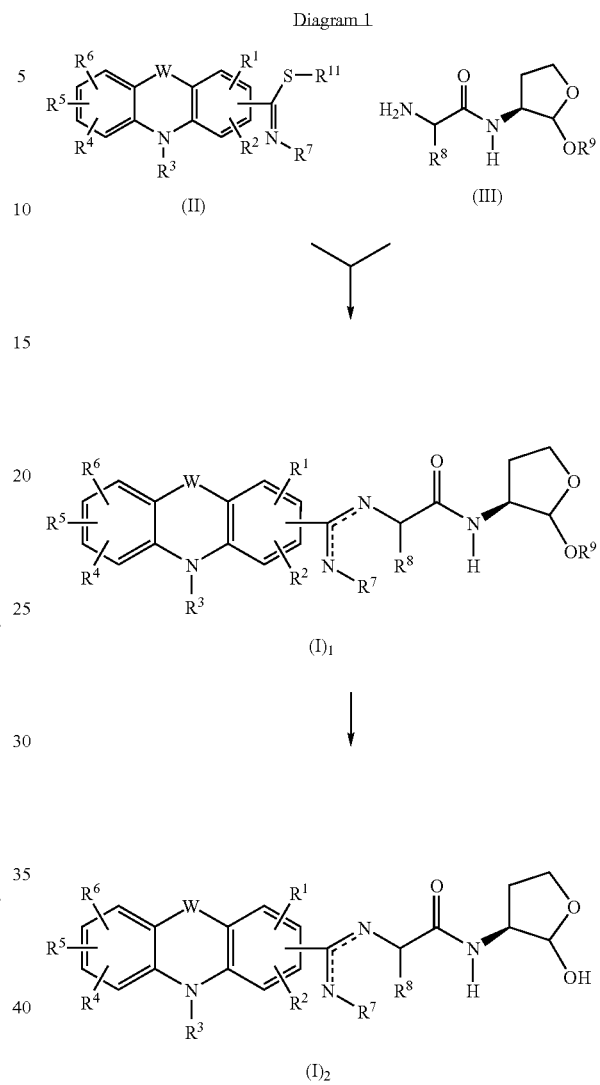

The compounds of general formulae $(I)_1$ and $(I)_2$ are obtained according to Diagram 1 by condensation of the thioimidates derivatives of general formula (II) with the amino-lactols of general formula (III), preferably by heating between 25 and 60° C., preferentially in a polar solvent, such as for example isopropanol, DMF or even THF, for a period of 4 to 20 hours. The hemiacetal function of the compounds of general formula $(I)_1$ can then be deprotected in order to produce the compound of general formula $(I)_2$, for example in an acid medium, using an inorganic acid such as HCl or HBr or an organic acid, such as for example benzene sulphonic acid, in solution in an organic solvent such as for example acetone, THF, dioxane, acetonitrile or ethanol. The reaction is carried out generally at about 20° C. and for a time varying from 4 to 20 hours according to the nature of $R^9$.

Preparation of the Intermediates of General Formula (II):

The non commercial thioimidates of general formula (II), in which W, $R^1$, $R^2$, $R^3$, $R^4$, $R^5$, $R^6$ and $R^7$ are as described above in the description, can be prepared according to the synthetic route detailed in Diagram 2.

Diagram 2

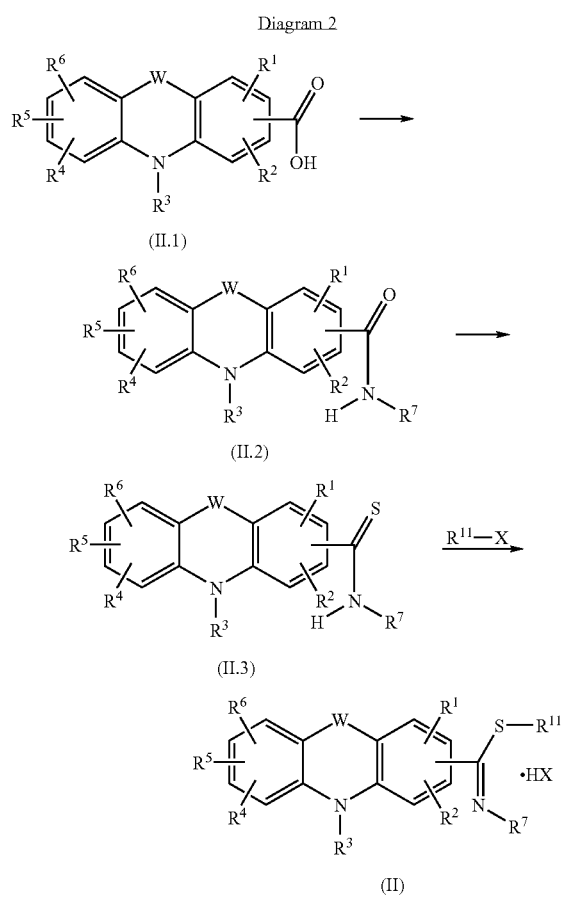

Preparation of the Intermediates of General Formula (III):

The amino-lactol derivatives of general formula (III), in which $R^8$ and $R^9$ are as described above, with Gp being a protective group preferably of the carbamate type, are accessible by using, for example, the preparation routes shown in Diagram 3 below.

Diagram 3

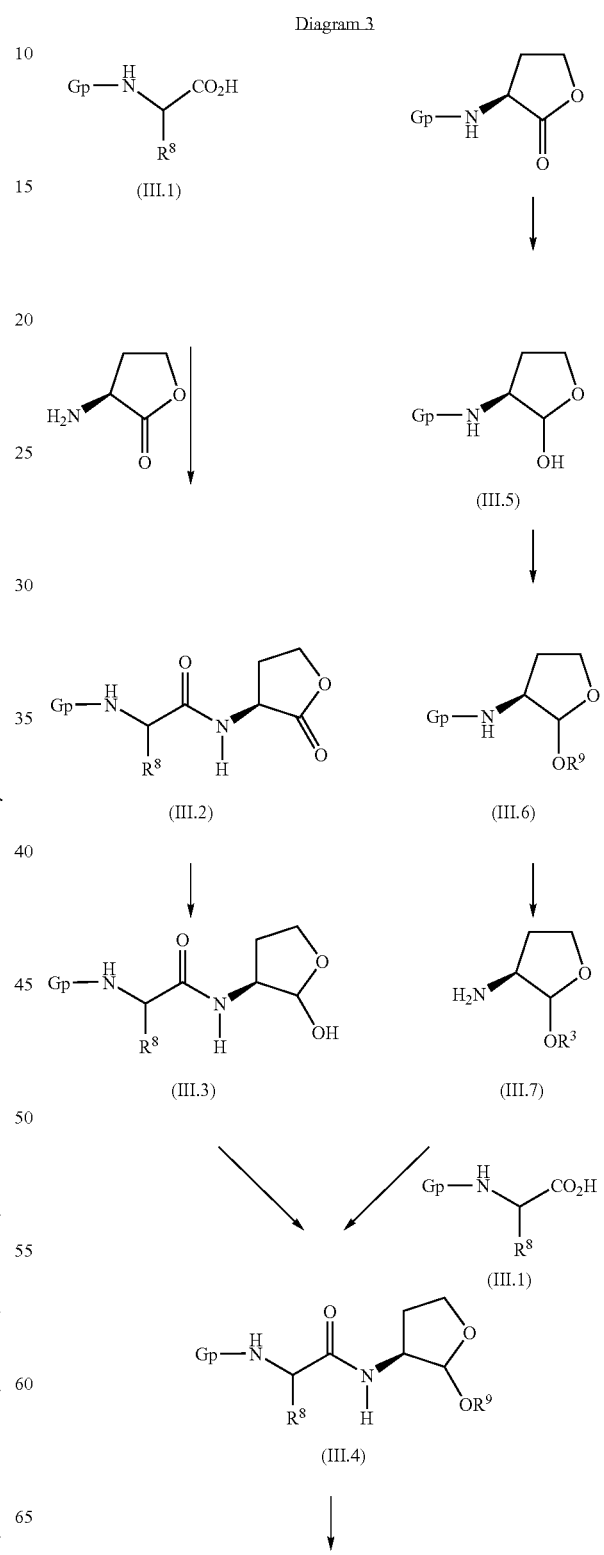

The thioimidates of general formula (II), derivatives of phenothiazine (W=S), phenoxazine (W=O) or carbazole (—W— is a bond) can be obtained in 3 stages starting from the corresponding carboxylic acids of general formula (II.1). These carboxylic acids are accessible from methods described in the literature such as, for example, *Pharmazie* 1984, 39(1), 22-3; *Bull. Soc. Chim.* 1968, (7), 2832-42, *Pharmazie* 1966, 21(11), 645-9, *Synthesis* 1988, (3), 215-17, *J. Med. Chem.* 1992, 35(4), 716-24, *J. Org. Chem.* (1960), 25, 747-53, *Heterocycles* (1994), 39(2), 833-45; *J. Indian Chem. Soc.* (1985), 62(7), 534-6; *J. Chem. Soc. Chem. Comm.* (1985), (2), 86-7. The formation of the carboxamides of general formula (II.2) is carried out in the presence of a concentrated aqueous solution of ammonia ($R^7$=H) or even an amine ($R^7$=alkyl), using a peptide coupling reactant, such as for example DCC or HBTU, in a solvent such as, for example, DMF. The thiocarboxamides of general formula (II.3) can be carried out by the action of Lawesson reactant in solution in 1,4-dioxane. The alkylation of the thiocarboxamides to generate the thioimidates of general formula (II) can be performed using $R^{11}$—X, X being a leaving group such as for example a halogen atom, a sulphate or triflate group. The reaction mixture is for example stirred in acetone for 15 hours. The thioimidates (II) are obtained in the form of salts, for example, hydroiodide if iodomethane ($R^{11}$—X) is used, and can optionally be desalified using a base such as, for example, sodium carbonate.

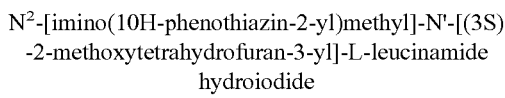

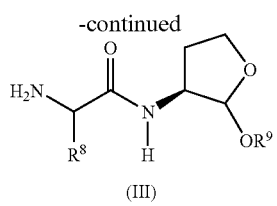

(III)

The amino-butyrolactone derivatives of general formula (III.2) can be obtained by condensation of the protected aminoacids of general formula (III.1), in which $R^8$ is an amino acid radical as defined previously in general formula (I) and Gp is a protective group such as, for example, a benzyl, tert-butyl or fluorenylmethyl carbamate, with (S)-α-aminobutyrolactone under standard conditions for peptide synthesis in order to produce the carboxamide intermediates of general formula (III.2). The lactone (III.2) is then reduced to lactol using a reducing agent such as, for example, diisobutylaluminium hydride (DIBAL), in an inert solvent such as, for example, THF or $CH_2Cl_2$, at a temperature preferably below −50° C., for example, approximately −78° C. The hemiacetal function of the lactol derivatives of general formula (III.3) is then protected either in an alcohol medium, for example in methanol or benzyl alcohol, using a strong acid such as, for example, trifluoroacetic or camphorsulphonic acid, or in the presence of a carboxylic acid anhydride, for example acetic anhydride, in the presence of 4-dimethylaminopyridine in an inert solvent, such as dichloromethane, in order to produce the acetals of general formula (III.4), Alternatively, the amino-lactols of general formula (III), can be prepared in 5 stages starting from commercial protected (S)-α-aminobutyrolactones. The successive stages of reduction of the lactone and protection of the hemiacetal in order to produce the intermediates (III.5) and (III.6) are identical to those described for generation of the intermediates (III.3) and (III.4). The preparation of the intermediates (III.7) is carried out preferably by hydrogenolysis, in the presence of Pd/C, of the benzyloxycarbonyl group principally used in this strategy. The intermediates of general formula (III.4) can then be obtained by peptide condensation under the conditions described above for (III.2), between the intermediates (III.7) and the aminoacids of general formula (III.1). The amine function of the intermediates of general formula (III.4) is then deprotected according to the methods described in the literature (T. W. Greene and P. G. M. Wuts, Protective Groups in Organic Synthesis, Second edition (Wiley-Interscience, 1991)).

Unless defined otherwise, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are given to illustrate the procedures above and should in no way be considered as limiting the scope of the invention.

EXAMPLES

The terminology used for the nomenclature of the examples below is the English IUPAC terminology.

In the following examples, the melting points were measured by means of a capillary using a device with the trade name Büchi, model B-545.

Example 1

$N^2$-[imino(10H-phenothiazin-2-yl)methyl]-N'-[(3S)-2-methoxytetrahydrofuran-3-yl]-L-leucinamide hydroiodide 1.1) $N^2$-[(benzyloxy)carbonyl]-N'-[(3S-2-oxotetrahydrofuran-3-yl]-L-leucinamide 3.51 g (13.25 mmol) of Cbz-L-Leucine, 2.41 g (1 eq.) of (S)-2-amino-4-butyrolactone hydrobromide, 1.97 g of HOBT (1.1 eq.) and 5.59 g (2.2 eq.) of −1-(3-dimethylaminopropyl)-3-ethyl carbodiimide hydrochloride (EDC) are dissolved in 60 ml of anhydrous DMF, then 7.64 ml of (3.3 eq.) of N,N-diisopropylethylamine is added. The reaction mixture is stirred for 15 hours at 20° C. before of being poured into 200 ml of a 1/1 mixture of ethyl acetate/water. After stirring and decantation, the organic solution is washed successively with 100 ml of a saturated solution of $NaHCO_3$, 50 ml of water, 100 ml of a 1M solution of citric acid and finally 100 ml of a solution of salt water. The organic phase is dried over sodium sulphate, filtered and concentrated to dryness under vacuum. The oil obtained is washed using isopentane and then crystallized from a dichloromethane/isopentane mixture. A white solid is obtained with a yield of 68%.

Melting point: 130-131° C.

1.2) $N^2$-[(benzyloxy)carbonyl]-$N^1$-[(3S)-2-hydroxytetrahydrofuran-3-yl]-L-leucinamide 1.24 g (3.56 mmol) of intermediate 1.1 is dissolved under argon in a three-necked flask containing 60 ml of anhydrous dichloromethane. The mixture is cooled down to −60° C. before 10.7 ml of (3 eq.) of a 1M solution of DIBAL in dichloromethane is added dropwise. At the end of the addition, the cooling bath is removed and stirring is maintained for an additional 15 minutes. The reaction medium is then carefully poured into 100 ml of a 20% Rochelle salt solution. After 2 hours of vigorous stirring, 100 ml of dichloromethane is added and the whole is poured into a separating funnel. The organic phase is recovered and washed with 50 ml of water and 50 ml of salt water. After drying over sodium sulphate and filtration, the organic solution is concentrated to dryness under vacuum. The evaporation residue is purified using a silica column (eluent: heptane/AcOEt: 1/1 up to 2/8). A white solid with a yield of 72% is obtained. Melting point: 48-49° C.

1.3) $N^2$-[(benzyloxy)carbonyl]-$N^1$-[(3S)-2-methoxytetrahydrofuran-3-yl]-L-leucinamide An excess of trifluoroacetic acid (5 ml) is added dropwise at 20° C. to a solution of 0.82 g (2.34 mmol) of the intermediate 1.2 in 50 ml of methanol. Stirring is maintained for 15 hours at 20° C. The reaction mixture is then partially concentrated under vacuum and redissolved in 50 ml of dichloromethane. The organic solution is washed successively with 50 ml of a saturated solution of $NaHCO_3$, 50 ml of water and 50 ml of salt water. After drying over sodium sulphate, filtration and concentration under vacuum, the evaporation residue is purified using a silica column (eluent: heptane/AcOEt: 1/1 up to 3/7). A white solid is obtained with a yield of 80%. Melting point: 112-113° C.

1.4) $N^1$-[(3S)-2-methoxytetrahydrofuran-3-yl]-L-leucinamide 2 g (5.5 mmol) of intermediate 1.3 and 600 mg of Pd/C at 10% are introduced into a stainless steel reactor containing 60 ml of methanol. The mixture is stirred under 2 atm. hydrogen pressure for 1 hour. After filtration of the catalyst, the methanol is evaporated off under vacuum. The oily residue obtained (1.20 g; 94%) is used as it is in the following stage.

1.5) 10H-phenothiazine-2-carbothioamide

A reaction mixture comprising 3.4 g (14 mmoles) of 10H-phenothiazine-2-carboxamide (*J. Org. Chem.* 1961, 26, 1138-1143) and 3.4 g (8.4 mmoles) of Lawesson reagent in solution in 40 ml of 1,4-dioxane to which 20 ml of pyridine has been added is heated to 110° C. for 1 h 30. The brown solution is then concentrated under vacuum and the residue is diluted in 200 ml of AcOEt and 100 ml of $H_2O$. After stirring and decantation, the organic phase is washed successively with 100 ml of a 1N aqueous solution of HCl and 100 ml of salt water. After drying over sodium sulphate, filtration and evaporation of the solvent under vacuum, an orange powder is obtained. This powder is washed with $Et_2O$, the filtrate is eliminated, and extracted with acetone. The acetone filtrate is then concentrated under vacuum and the evaporation residue is then purified using a silica column (eluent: Heptane/AcOEt: 1/1 to 4/6). Orange powder. Melting point: 208-209° C.

1.6) Methyl 10H-phenothiazine-2-carbimidothioate hydroiodide 0.3 ml (1.2 eq.) of iodomethane is added at 23° C. to a solution of 1.05 g (4.1 mmoles) of intermediate 1.5 in 10 ml of acetone. The reaction mixture is stirred for 15 hours. The precipitate formed is filtered and rinsed successively with acetone and isopentane. A brown-violet solid is obtained with a yield of 85%. Melting point: 207-208° C.

1.7) $N^2$-[imino(10H-phenothiazin-2-yl)methyl]-$N^1$-[(3S)-2-methoxytetrahydrofuran-3-yl]-L-leucinamide hydroiodide 1.18 g (1 eq.) of intermediate 1.6 is added to a solution of 0.68 g (2.95 mmoles) of intermediate 1.4 in 20 ml of isopropanol. The reaction mixture is stirred at 60° C. for 15 hours. The methanethiol released during the reaction is successively trapped using a solution of soda and a solution of potassium permanganate. The solid formed is isolated by filtration and rinsed with $Et_2O$ before of being purified using a silica column (eluent; heptane/AcOEt; 1/1 to 0/1). An orange solid is obtained with a yield of 70%. Melting point: 155-165° C.

Example 2

$N^1$-[(3S)-2-(benzyloxy)tetrahydrofuran-3-yl]-$N^2$-[imino(10H-phenothiazin-2-yl)methyl]-L-leucinamide hydroiodide

2.1) $N^2$-[(9H-fluoren-9-ylmethoxy)carbonyl]-N-[(3S)-2-oxotetrahydrofuran-3-yl]-L-leucinamide The experimental protocol used is the same as that described for the synthesis of intermediate 1.1, Fmoc-L-Leucine replacing Cbz-L-Leucine. 3.15 g of a white solid is obtained by crystallization from AcOEt with a yield of 72%. Melting point: 175-176° C.

2.2) $N^2$-[(9H-fluoren-9-ylmethoxy)carbonyl]-N'-[(3S)-2-hydroxytetrahydrofuran-3-yl]-L-leucinamide The experimental protocol used is the same as that described for the synthesis of intermediate 1.2, with intermediate 2.1 replacing intermediate 1.1. After purification on a silica column (heptane/AcOEt: 1/1), 2.16 g white solid is obtained with a yield of 68%. Melting point: 155-156° C.

2.3) $N^1$-[(3S)-2-(benzyloxy)tetrahydrofuran-3-yl]-$N^2$-[(9H-fluoren-9-ylmethoxy)carbonyl]-L-leucinamide 0.41 ml (1.1 eq.) of benzyl alcohol and 0.11 g (0.13 eq.) of camphorsulphonic acid are added to a suspension of 1.57 g (3.58 mmoles) of intermediate 2.2 in 7 ml of dichloromethane. As the reaction proceeds, the reaction medium becomes homogeneous. After stirring for 24 hours, the mixture is diluted with 25 ml of water and 25 ml of dichloromethane, stirred and decanted. The organic solution is dried over sodium sulphate, filtered and concentrated to dryness. The residue is purified using a silica column (heptane/AcOEt: 1/0 to 1/1). After evaporation, 1.43 g white solid is obtained with a yield of 76%. Melting point: 116-117° C.

2.4) $N^1$-[(3S)-2-(benzyloxy)tetrahydrofuran-3-yl]-L-leucinamide 0.2 ml (5 eq.) of diethylamine is added dropwise to a solution of 0.2 g (0.38 mmol) of intermediate 2.3 in solution in 3.5 ml of dichloromethane. The reaction mixture is stirred at 23° C. for 5 h 30 before being concentrated to dryness under vacuum. The residue is partially redissolved with $Et_2O$ and stored at 4° C. for a few hours. The white precipitate formed is eliminated by filtration and the filtrate is concentrated to dryness. The evaporation residue is used as it is in the following stage.

2.5) $N^1$-[(3S)-2-(benzyloxy)tetrahydrofuran-3-yl]-$N^2$-[imino(10H-phenothiazin-2-yl)methyl]-L-leucinamide hydroiodide The experimental protocol used is the same as that described for the synthesis of intermediate 1.7, by reaction of intermediate 1.6 with intermediate 2.4 which is used in place of intermediate 1.4. The product of the reaction is purified using a silica column (heptane/AcOEt:1/1 to 0/1). After evaporation of the purest fractions, the residue is mixed in isopentane/AcOEt in order to produce a pale orange precipitate. 430 mg of the expected product is obtained with a yield of 53%. Melting point: 140-145° C.

Example 3

$N^2$-[imino(10H-phenothiazin-2-yl)methyl]-$N^1$-[(3S)-2-(2-naphthylmethoxy)tetrahydrofuran-3-yl]-L-leucinamide hydroiodide

3.1) $N^2$-[(9H-fluoren-9-ylmethoxy)carbonyl]-N'-[(3S)-2-(2-naphthylmethoxy) tetrahydrofuran-3-yl]-L-leucinamide The experimental protocol used is the same as that described for the synthesis of intermediate 2.3 starting from intermediate 2.2 and 2-hydroxymethylnaphthalene is used in place of the benzyl alcohol. After purification on a silica

3.2) N¹-[(3S)-2-(2-naphthylmethoxy)tetrahydrofuran-3-yl]-leucinamide

The experimental protocol used is the same as that described for the synthesis of intermediate 2.4, with intermediate 3.1 replacing intermediate 2.3. The product is obtained after elimination of the dibenzofulvene derivatives and is used as it is in the following stage.

3.3) N²-[imino(10H-phenothiazin-2-yl)methyl]-N¹-[(3S)-2-(2-naphthyl methoxy)tetrahydrofuran-3-yl]-L-leucinamide hydroiodide The experimental protocol used is the same as that described for the synthesis of intermediate 1.7, starting from intermediate 1.6 and intermediate 3.2 used in place of intermediate 1.4. The product of the condensation reaction is purified using a silica column (heptane/AcOEt; 1/1 to 0/1). After evaporation of the purest fractions, the residue is mixed in isopentane/AcOEt in order to produce an orange precipitate, 530 mg of the expected product is obtained with a yield of 64%. Melting point, 145-148° C.

Example 4

4.1)(3S)-3-({N-[imino(10H-phenothiazin-2-yl)methyl]-L-leucyl}amino)tetrahydrofuran-2-yl acetate hydroiodide

4.1) (3S)-3-({N-[(benzyloxy)carbonyl]-L-leucyl}amino)tetrahydrofuran-2-yl acetate 2 g (5.73 mmoles) of intermediate 1.2 and 0.14 g (0.2 eq.) of 4-dimethylaminopyridine are dissolved, under an argon atmosphere, in 13 ml of anhydrous dichloromethane. 5.4 ml (10 eq.) of acetic anhydride is added dropwise to this solution. After 5 hours of stirring at 23° C., the reaction mixture is diluted with 50 ml of dichloromethane and 50 ml of water. The organic phase is then washed successively with 50 ml of a saturated solution of NaHCO₃, 50 ml of water and finally salt water. The dichloromethane solution is dried over Na₂SO₄, filtered and concentrated to dryness under vacuum. The residue obtained is mixed with Et₂O, filtered and rinsed with isopentane. 1.14 g white solid is obtained with a yield of 50%. Melting point: 158-159° C.

4.2) (3S)-3-(L-leucylamino)tetrahydrofuran-2-yl acetate 1.14 g (2.89 mmoles) of intermediate 4.1 and 227 mg of Pd/C at 10% are introduced into a stainless steel reactor containing 30 ml of acetic acid. The mixture is stirred under 2 atm. hydrogen pressure for 4 h 30. After filtration of the catalyst, the acetic acid is evaporated off under vacuum. The oily residue obtained is divided between 50 ml of dichloromethane and 50 ml of a saturated NaHCO₃ solution. Stirring and decantation are followed by washing the organic phase with water and salt water. After drying over Na₂SO₄, filtration and concentration to dryness the colourless oil obtained crystallizes spontaneously in order to produce 0.45 g of a white solid with a yield of 60%. Melting point: 75-80° C.

4.3) (3S)-3-({N-[imino(10H-phenothiazin-2-yl)methyl]-L-leucyl}amino) tetrahydrofuran-2-yl acetate hydroiodide The experimental protocol used is the same as that described for the synthesis of intermediate 1.7, starting from intermediate 1.6 and intermediate 4.2 with the exception of the reaction solvent which in this case is THF, and the heating time which is limited to 4 hours. The reaction mixture is directly adsorbed on silica and deposited at the top of a chromatography column (heptane/AcOEt:: 3/7 up to 0/1) for purification. After collection and evaporation of the pure fractions, 0.27 g orange solid is obtained with a yield of 18%. Melting point: 130-131° C.

Example 5

N¹-[(3S)-2-hydroxytetrahydrofuran-3-yl]-N²-[imino(10H-phenothiazin-2-yl)methyl]-L-leucinamide hydroiodide 12 mg (0.1 eq.) of benzenesulphonic acid is added to a solution of 0.42 g (0.69 mmole) of intermediate 4.3 in 42 ml of THF, at 23° C. After 5 h 30 of stirring at 23° C., 137 µl of a 0.5 M solution of NaHCO₃ (0.1 eq.) is added. Stirring is maintained for 5 another minutes before filtration of the precipitate formed. The filtrate is concentrated to dryness and the residue is purified using a silica column (dichloromethane/EtOH: 95/5 to 90/10). The pure fractions are collected and evaporated in order to produce 171 mg of an orange solid with a yield of 43%. Melting point: 148-150° C.

Example 6

6.1) N-ethyl-10H-phenothiazine-2-carboxamide 5.8 ml (3.3 eq.) of DIEAA is added dropwise to a solution of 2.43 g (10 mmoles) of 10H-phenothiazine-2-carboxylic acid, 1.79 g (2.2 eq.) of ethylamine hydrochloride and 4.17 g (1.1 eq.) of HBTU in 50 ml of DMF, cooled down to 0° C. The reaction mixture is stirred for 15 hours at 23° C., and then poured into a mixture of 100 ml of a saturated solution of NaHCO₃ and 100 ml of AcOEt. After stirring for a few minutes, the precipitate formed is removed by filtration and the filtrate is decanted. The organic phase is successively washed with water, a 1M solution of citric acid and salt water. The organic solution is dried over sodium sulphate, filtered and concentrated to dryness under vacuum. The solid obtained is suspended in Et₂O, triturated and filtered. A beige solid is obtained with a quantitative yield. Melting point: 150-151° C.

6.2) N-ethyl-10H-phenothiazine-2-carbothioamide

The experimental protocol used is the same as that described for intermediate 1.5, with intermediate 6.1 replacing 10H-phenothiazine-2-carboxamide. 2.17 g of a yellow solid is obtained with a yield of 60%. Melting point: 155-156° C.

6.3) Methyl N-ethyl-10H-phenothiazine-2-carbimidothioate hydrochloride

The experimental protocol used is the same as that described for intermediate 1.6 using iodomethane, intermediate 6.2 replacing intermediate 1.5. The salified compound obtained in hydroiodide form is then divided between a saturated solution of NaHCO$_3$ and AcOEt. After decantation, the organic phase is washed with water and salt water, dried over sodium sulphate and filtered. 1.1 eq. of a 1N titrated solution of HCl in anhydrous Et$_2$O is then added to this cooled organic solution at 0° C. After stirring for one hour at 23° C., the reaction mixture is concentrated to dryness under vacuum. The evaporation residue is finally suspended in Et$_2$O and filtered. A dark red solid is obtained. Melting point: 142-143° C., Pharmacological Study of the Compounds of the Invention:
All percentages are given by volume.

Effect In Situ of the Compounds According to the Invention on the Calpain Enzymatic Activity of Human Skeletal Cells (SKM)

The principle of the test is the following: maitotoxin is a toxin which causes the opening of the calcium channels of cells. The resulting intra-cellular flow of calcium is at the origin of the death of the cell. During this process of cell death, a cysteine-dependent protease, calpain, is activated. The test consists of incubating the cells in the presence of maitotoxin, in order to activate the calpain enzyme, and adding a calpain substrate which fluoresces when the enzyme cleaves this substrate. Finally, calpain inhibitors are tested.

The myoblasts are seeded at 2500 cells per well in 96-well plates in a DMEM 10% FCS (foetal calf serum) culture medium supplemented with amphotericin B, human recombinant epidermal growth factor and dexamethasone. Three days after seeding, the cells have adhered to the bottom of the well, the differentiation of the cells to myotubes is induced by adding 100 µl of DMEM F12 medium containing 2% horse serum. After three more days, 100 µl of the test compound are placed at the bottom of the well. After incubation for one hour at 37° C. under an atmosphere of 5% CO$_2$, the fluorescent substrate of the calpain (Suc-Leu-Tyr-AMC) and the maitotoxin (MTX) (Sigma, ref: M-9159) are added. In order to determine the total activity of the cellular enzyme, control wells without test compounds are prepared on the plate (100 µl DMSO diluted to 100$^{th}$ to which 10 µl of MTX and substrate are added). The background noise is determined by preparing additional control wells without MTX. Each concentration of the products is tested in triplicate. The plates are stirred, the fluorescence is read at 380/460 nm using a so-called Victor device at time zero. The incubation takes place for three hours at 30° C. in darkness.

The fluorescence values make it possible to calculate a concentration-effect for each of the compounds. The IC$_{50}$ (concentration of the tested substance which inhibits 50% of the enzyme activity) is calculated from this concentration-effect.

The compound of Example 5 has an IC$_{50}$ below 20 µM in this test.

Study of the Effects on Lipidic Peroxidation in the Cerebral Cortex of the Rat

The inhibitory activity of the products of the invention is determined by measuring their effects on the degree of lipidic peroxidation, determined by the concentration of malondialdehyde (MDA). The MDA produced by the peroxidation of unsaturated fatty acids is a good indicator of lipidic peroxidation (H Esterbauer and K H Cheeseman, *Meth. Enzymol.* (1990) 186: 407-421). Male Sprague Dawley rats weighing 200 to 250 g (Charles River) were sacrificed by decapitation. The cerebral cortex is removed, then homogenised with a Thomas potter in a Tris-HCl buffer, 20 mM, pH=7.4. The homogenate is centrifuged twice at 50,000 g for 10 minutes at 4° C. The pellet is kept at −80° C. On the day of the experiment, the pellet is resuspended at a concentration of 1 g/15 ml and centrifuged at 515 g for 10 minutes at 4° C. The supernatant is used immediately to determine lipidic peroxidation. The homogenate of rat cerebral cortex (500 µl) is incubated at 37° C. for 15 minutes in the presence of the compounds to be tested or of the solvent (10 µl). The lipidic peroxidation reaction is initiated by adding 50 µl of FeCl$_2$ at 1 mM, EDTA at 1 mM and ascorbic acid at 4 mM. After incubation for 30 minutes at 37° C., the reaction is stopped by adding 50 µl of a solution of hydroxylated di-tert-butyl toluene (BHT, 0.2%) The MDA is quantified using a calorimetric test, by reacting a chromogenic reagent (R), N-methyl-2-phenylindole (650 µl), with 200 µl of the homogenate for 1 hour at 45° C. Condensation of a molecule of MDA with two molecules of reagent R produces a stable chromophore the maximum absorbance wavelength of which is equal to 586 nm. (Caldwell et al., *European J. Pharmacol.* (1995), 285, 203-206).

The compounds of Examples 1 to 5 have an IC$_{50}$ below 5 µM in this test.

Protective Effect of the Compounds According to the Invention on Cell Death Induced by Maitotoxin on Human Skeletal Cells (SKM)

The principle of the test is the following: maitotoxin is a toxin which causes the opening of the calcium channels of cells. The resulting intra-cellular flow of calcium is at the origin of the death of the cell. During this process of cell death, a cysteine-dependent protease, calpain, is activated, and an abundance of free radicals is produced. The test consists of incubating the cells in the presence of the molecules to be tested, in order to delay or inactivate cell death and thus determine the protective effect.

The myoblasts are seeded at 2500 cells per well in 96-well plates in a DMEM 10% FCS (foetal calf serum) culture medium supplemented with amphotericin B, human recombinant epidermal growth factor and dexamethasone. Three days after seeding, the cells have adhered to the base of the well, the differentiation of the cellules to myotubes is induced by adding 100 µl of DMEM F12 medium containing 2% horse serum. After three more days, 100 µl of compound to be tested are placed at the bottom of the well. After incubation for one hour at 37° C. under an atmosphere of 5% CO$_2$, the maitotoxin (MTX) (Wako, ref: 131-10731) is added to evaluate the protective effect (concentration-effect) of the compound to be tested on cell death.

After an incubation time of 3 h or 96 h, the culture medium is replaced by a DMEM 10% FCS medium supplemented by 10% WST-1, WST-1 (Roche, reference 1644807) is a reagent which stains metabolically active cells, i.e. live cells. The cells are incubated for 1 hour in the presence of WST-1. Then the number of live cells is determined using a Perkin-Elmer Wallac Envision 2101 device by reading the absorbance at 450 nm. The concentration-effect of the products on the cell survival fraction is then calculated.

The EC$_{50}$ (concentration of the test substance which protects 50% of the cells from cell death) is calculated from this concentration-effect.

The compound of Example 5 in this test has an EC$_{50}$ below 16.4 µM after incubation for 3 hours in the presence of maitotoxin, and 18.3 µM after incubation for 96 hours in the presence of maitotoxin.

A comparative test is carried out with a-methylprednisolone which is a compound used for the treatment of Duchenne's muscular dystrophy. In comparison, with the same test and under the same conditions, a-methylprednisolone has an $EC_{50}$ of 354.3 µM after incubation for 3 hours in the presence of maitotoxin, and 195.7 µM after incubation for 96 hours in the presence of maitotoxin.

Ototoxicity Induced after a Treatment with Gentamycin: Protective Effect of the Compounds According to the Invention Demonstration of the protective effect of the compounds according to the invention, administered as a co-treatment, vis-á-vis the loss of ciliated cells induced by gentamycin.

Principle of the test: gentamycin and other aminoglycosides cause damage to ciliated cells and a hearing loss in humans. Zebrafish have sensory organs known as neuromasts on the surface of their body. These neuromast ciliated cells are structurally and functionally similar to the internal ciliated cells of the human ear. In these fish, the neuromast ciliated cells can be stained with DASPEI (2,4-dimethyl-aminostyryl-N-ethyl pyridinium iodide) and this staining reflects the number of functional ciliated cells.

Damage to the internal ciliated cells is induced in the Zebrafish with a gentamycin treatment. In order to test the protective effect of the compound to be tested on ciliated cells damaged by gentamycin, the compound was administered as a co-treatment with gentamycin. The internal ciliated cells are then stained and quantified.

The study is carried out on 5-day old fish, incubated with 1 µg/ml of gentamycin for 24 hours in the presence or the absence of the compound. Controls are carried out in parallel; vehicle alone (1% DMSO; positive control). Fish treated with gentamycin only are the negative controls.

The $EC_{50}$ (concentration of the substance to be tested which protects 50% of the cells from cell death) is calculated from this concentration-effect.

The DASPEI staining is carried out to visualize the ciliated cells in vivo (n=6 per group). Morphometric analysis is used to quantify the staining signal of the ciliated cells. The DASPEI staining signal of the positive controls was defined as 100%.

The results of Table 1 show that:

The staining signal of the negative control represents 20%+/−0.6 of the control signal, i.e. a loss of 80% of the ciliated cells following treatment with gentamycin.

The staining signal of the animals treated with gentamycin and the compound of Example 5 tested at 50 µM represents 52%+/−10 of the control signal, i.e. a highly significant protection of 40% of the ciliated cells damaged by the gentamycin treatment. Over a range of concentrations from 25 µM to 100 µM, the $EC_{50}$ which corresponds to the effective concentration which allows 50% of stained cells to be visualized is 32 µM.

The staining signal of the animals treated with gentamycin and the compound of Example 4 at 50 µM represents 49%+/−5 of the control signal, i.e. a highly significant protection of 36.2% of the ciliated cells damaged by the gentamycin treatment. Over a range of concentrations from 25 µM to 100 µM, the $EC_{50}$ which corresponds to the effective concentration which allows 50% of stained cells to be visualized is 51 µM.

TABLE 1

Table 1: Percentage of ciliated cells stained by DASPEI

| Compound Control | [C] | control % (% staining signal of the ciliated cells) | Statistical Significance (P Value) | $EC_{50}$ µM (survival of the ciliated cells in % of the control) (0, 25, 50, 100 µM) |
|---|---|---|---|---|
| Gentamycin | 1 µg/ml | 20 ± 0.6 | | |
| Compound of Example 5 | 50 µM | 52 ± 10 | <0.0005 * | 32 µM |
| Compound of Example 4 | 50 µM | 49 ± 5 | <0.0005 * | 51 µM |

Positive control (Zebrafish-1% DMSO); Negative control (Zebrafish-1% DMSO-gentamycin 1 µg/ml) and effect of the products (Zebrafish-1% DMSO-gentamycin-compound). Experiment carried out on 6 animals per group.

The invention claimed is:

1. A compound of formula (i) or its salt

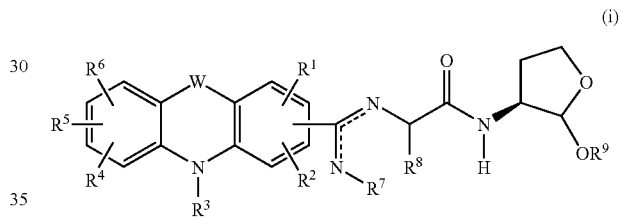

(i)

in which:

$R^1$, $R^2$, $R^4$, $R^5$ and $R^6$ represent, independently, a hydrogen atom, halogen atom, the OH group, an alkyl, alkoxy, cyano, nitro, amino, alkylamino radical or carboxylic acid;

$R^3$ represents a hydrogen atom, an alkyl radical or a —$COR^{10}$ group;

$R^{10}$ represents a hydrogen atom or an alkyl, alkoxy, aryl radical, or a heterocyclic radical;

W represents sulfur atom;

$R^7$ represents a hydrogen atom or an alkyl radical;

$R^8$ represents a hydrogen atom, a haloalkyl or alkenyl radical, a cycloalkyl radical, a linear or branched alkyl radical, optionally substituted with carboxylic acid, amino, alcohol, guanidine, amidine, thiol, thioether, thioester, alkoxy, heterocyclic or carboxamide;

$R^9$ represents a hydrogen atom, an alkyl, aryl, arylalkyl, bisarylalkyl radical, a heterocyclic radical, a heterocyclic alkyl radical or a —$COR^{10}$ group;

with the proviso that:

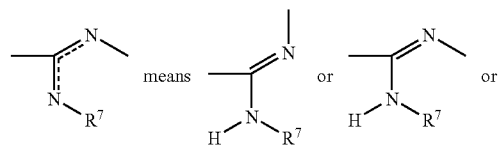

-continued

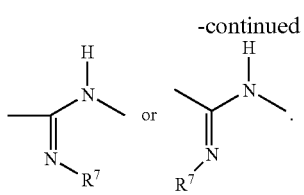

2. The compound according to claim 1, wherein $R^1$ is a hydrogen atom.
3. The compound according to claim 1, wherein $R^2$ is a hydrogen atom.
4. The compound according to claim 1, wherein $R^3$ is a hydrogen atom.
5. The compound according to claim 1, wherein $R^4$ is a hydrogen atom.
6. The compound according to claim 1, wherein $R^5$ is a hydrogen atom.
7. The compound according to claim 1, wherein $R^6$ is a hydrogen atom.
8. The compound according to claim 1, wherein $R^7$ is a hydrogen atom.
9. The compound according to claim 1, wherein $R^8$ is an isobutyl radical.
10. The compound according to claim 1, wherein $R^9$ is a hydrogen atom.
11. The compound according to claim 1, wherein $R^9$ is an acetyl radical.
12. The compound according to claim 1, wherein $R^9$ is a methyl radical.
13. The compound according to claim 1, wherein $R^9$ is a benzyl radical.
14. The compound according to claim 1, wherein $R^9$ is a naphthylmethyl radical.
15. The compound according to claim 1, wherein the compound is:
   $N^2$-[imino(10H-phenothiazin-2-yl)methyl]-N'-[(3S)-2-methoxytetrahydrofuran-3-yl]-L-leucinamide;
   $N^1$-[(3S)-2-(benzyloxy)tetrahydrofuran-3-yl]-$N^2$-[imino(10H-phenothiazin-2-yl)methyl]-L-leucinamide;
   $N^2$-[imino(10H-phenothiazin-2-yl)methyl]-$N^1$-[(3S)-2-(2-naphthylmethoxy)tetrahydrofuran-3-yl]-L-leucinamide;
   (3S)-3-({N-[imino(10H-phenothiazin-2-yl)methyl]-L-leucyl}amino)tetrahydrofuran-2-yl acetate;
   $N^1$-[(3S)-2-hydroxytetrahydrofuran-3-yl]-$N^2$-[imino(10H-phenothiazin-2-yl)methyl]-L-leucinamide; or salts thereof.
16. A method for the treatment of hearing loss or muscular distrophies comprising administering a therapeutically active quantity of the compound according to claim 1 to a patient in need thereof.
17. The method of claim 16, wherein the method is for treatment of muscular dystrophies.
18. A pharmaceutical composition comprising at least one compound as defined in claim 1 and a pharmaceutically acceptable excipient.
19. A composition comprising the compound of claim 1 in racemic form.
20. A composition comprising the compound of claim 1 in diastereoisomeric form.
21. The method of claim 16, wherein the hearing loss is caused by presbycusis, acoustic trauma, or by administration of antibiotics, anti-cancer agents, non-steroidal anti-inflammatory agents, diuretics, anti-ulcer agents, or anticonvulsive agents.
22. The method of claim 17, wherein the muscular dystrophy includes Duchenne's muscular dystrophy, Becker's muscular dystrophy, myotonic muscular dystrophy or Steiner's disease, congenital muscular dystrophy, limb girdle muscular dystrophy, or facioscapulohumeral muscular dystrophy.
23. The compound of claim 1, wherein the salt is a pharmaceutically acceptable salt.
24. The compound of claim 23, wherein the pharmaceutically acceptable salt is a hydrochloride, hydrobromide, hydroiodide, sulfate, phosphate, diphosphate, nitrate, acetate, maleate, fumarate, tartrate, succinate, citrate, lactate, methansulphonate, p-toluenesulphonate, benzenesulphonate, pamoate, or stearate.
25. The compound according to claim 1, wherein the compound is (3S)-3-({N-[imino(10H-phenothiazin-2-yl)methyl]-L-leucyl}amino)tetrahydrofuran-2-yl acetate, or a salt thereof.
26. The compound according to claim 1, wherein the compound is $N^1$-[(3S)-2-hydroxytetrahydrofuran-3-yl]-$N^2$-[imino(10H-phenothiazin-2-yl)methyl]-L-leucinamide, or a salt thereof.
27. The compound according to claim 16, wherein method is for treatment of hearing loss.

* * * * *